United States Patent [19]

Hibino et al.

[11] Patent Number: 5,095,120
[45] Date of Patent: Mar. 10, 1992

[54] PROCESS FOR THE PREPARATION OF PHOTOCHROMIC SPIROPYRAN COMPOUNDS

[75] Inventors: Junichi Hibino; Eiji Ando, both of Osaka, Japan

[73] Assignee: Matsushita Electric Industrial Co., Ltd., Japan

[21] Appl. No.: 570,469

[22] Filed: Aug. 21, 1990

[30] Foreign Application Priority Data

Aug. 21, 1989 [JP] Japan ................................ 1-214493

[51] Int. Cl.⁵ ........................................... C07D 405/02
[52] U.S. Cl. ..................................... 548/409; 548/454
[58] Field of Search ............................. 548/409, 454

[56] References Cited

U.S. PATENT DOCUMENTS 4,565,779  1/1986  Arakawa et al. ................... 548/590

OTHER PUBLICATIONS

Chemical Abstracts, vol. 88, No. 15, 10 Apr. 1978, Columbus, Ohio, U.S.A., E. R. Zakhs et al.
Chemical Abstracts, vol. 83, No. 17, 27 Oct. 1975, Columbus, Ohio, U.S.A., N. B. Samoilova.

*Primary Examiner*—David B. Springer
*Attorney, Agent, or Firm*—Lowe, Price, LeBlanc & Becker

[57] ABSTRACT

A process for preparing photochromic spiropyran compounds having a halogen atom or atoms and a hydrophobic alkyl group wherein a starting photochromic spiropyran compound having the hydrophobic alkyl group is reacted directly with a halogenating agent in a solvent. This reaction efficiently proceeds with the product being obtained in high yield.

12 Claims, No Drawings

PROCESS FOR THE PREPARATION OF PHOTOCHROMIC SPIROPYRAN COMPOUNDS

BACKGROUND OF THE INVENTION

1. Field of The Invention

This invention relates to a process for preparing photochromic spiropyran compounds having a long chain at the N position of the compound and a halogen atom or atoms at the indoline ring thereof.

2. Description of The Prior Art

Photochromic materials are known as those materials which undergo reversible changes in color. One of typical photochromic materials includes spiropyran compounds. A number of spiropyran compounds have been studied and developed up to now. For instance, a spiropyran compound of the following formula (A) is irradiated with UV light with a wavelength of 340 nm, whereupon it is changed into merocyanine of the formula (B) assuming a red color. When visible light with a wavelength of 580 nm is again applied to the merocyanine, it is returned to the spiropyran (A).

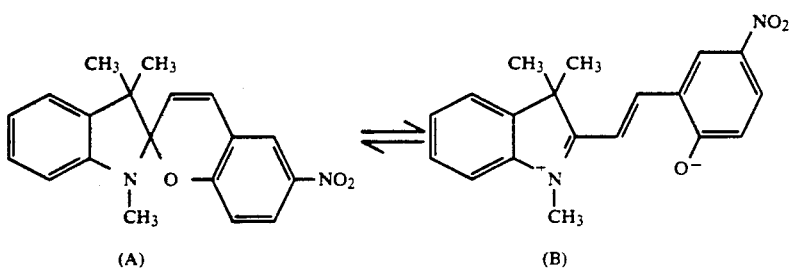

(A)     (B)

This property of the photochromic materials is suitable for application, for example, as optical recording media. In order to obtain high recording sensitivity and stability, the recording medium should preferably have a uniform, ultra-thin recording film. One of techniques of forming such a ultrathin film under mild conditions is the Langmuir-Blodgett technique (hereinafter referred to simply as LB technique or method).

For the formation of the thin film by the LB method, spiropyran compounds should favorably have a hydrophilic site or part and a hydrophobic site or part in the molecule. The spiropyran compounds without modification are so low in hydrophobicity that a satisfactory LB film cannot be formed. In most cases, the LB films of spiropyran compounds are formed after introducing a long alkyl chain at the N position of an indoline ring so that the hydrophilicity and hydrophobicity of the compound are well balanced.

A number of spiropyran compounds have been proposed using various structural backbones and substituents in combination. Among them, spiropyran compounds having an indoline ring substituted with a halogen atom or atoms have absorptions at long wavelengths when converted to colored products. Accordingly, such spiropyran compounds are suitable for recording with semiconductor laser devices and are very stable, thus exhibiting good recording characteristics and good reliability.

For the formation of an LB film of spiropyran compounds which have an indoline ring substituted with a halogen atom or atoms, it is essential to introduce a long hydrophobic chain at the N position of the ring. A typical known process of preparing spiropyran compounds having a long hydrophobic chain at the N position is a process wherein an alkyl halide is reacted with indolenine as shown in the following reaction formula

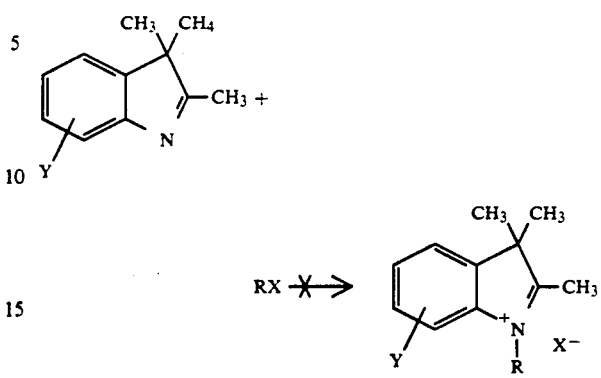

Because the alkyl halide having a long alkyl chain is low in reactivity, the reaction with a halogen-free indolenine of the above formulae where Y=H proceeds but the reaction with a haloindolenine of the formulae, where Y=F, Cl, Br or I, does not proceed at all or may proceed only under very severe conditions. The reason for this is that the activity of the indolenine is lowered due to the electrophilic property of the halogen atom.

Thus, it has not been possible in an industrial sense to prepare halogenated spiropyran compounds having a long chain according to the known process. Thus, a thin film of a halogenated spiropyran has not been obtained by the LB method.

SUMMARY OF THE INVENTION

It is accordingly an object of the invention to provide a process for preparing photochromic halogenated spiropyran compounds under mild reaction conditions at a high yield.

It is another object of the invention to provide a process for preparing photochromic halogenated spiropyran compounds which are suitable for forming a ultrathin film according to the LB method.

According to the invention, there is provided a process for preparing a photochromic halogenated spiropyran compound having a hydrophobic alkyl chain, the process comprising:

providing a photochromic spiropyran compound of the following formula (I)

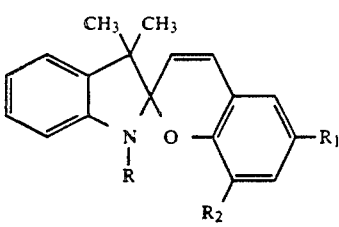

wherein R is an alkyl group having not less than 6 carbon atoms, and $R_1$ and $R_2$ independently represent hydrogen, a ketoalkyl, an alkoxy group, a nitro group, a halogen atom or an alkanoyloxymethyl group; and reacting a halogenating agent directly with the spiropyran compound to obtain a halogenated spiropyran photochromic compound of the following formula (II)

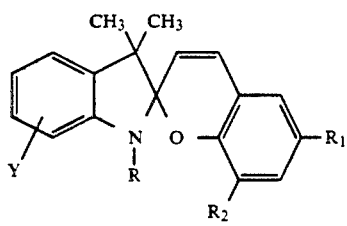

wherein R, $R_1$ and $R_2$ have, respectively, the same meanings as defined above and Y represents fluoride, chloride, bromine or iodine provided that one to four halogen atoms are substituted at the 4', 5', 6' and/or 7' position of the indoline ring.

In the above process, after introduction of a long chain into spiropyran compounds, a halogen atom or atoms are introduced into the compounds under mild conditions to obtain spiropyran compounds having a halogenated indoline ring at a high yield without impeding the characteristic properties of the compound. The compound can be formed into a thin film according to the LB method.

DETAILED DESCRIPTION AND EMBODIMENTS OF THE INVENTION

In the process of the invention, spiropyran compounds of the formula (I) are first provided.

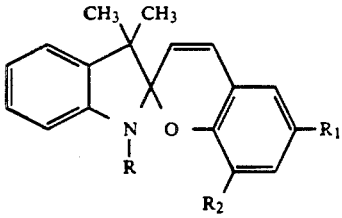

wherein R is an alkyl group, and $R_1$ and $R_2$ independently represent hydrogen, a ketoalkyl, an alkoxy group, a nitro group, a halogen atom or an alkanoyloxymethyl group. The alkyl group represented by R should have not less than 6 carbon atoms, preferably from 14 to 22 carbon atoms and more preferably 18 carbon atoms in view of the high amphoteric property and the ease in film formation. Specific examples of such alkyl group include a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, a octadecyl group, a nonadecyl group, an eicosyl group, a heneicosyl group, a docosyl group and the like.

$R_1$ and $R_2$ independently represent hydrogen, a ketoalkyl having from 2 to 18 carbon atoms, such as acetyl, octanoyl, octadecanoyl and the like, an alkoxy group having from 1 to 18 carbon atoms, such as methoxy to octadecanoxy groups, a nitro group, a halogen atom such as fluorine, chlorine, bromine or iodine, or an alkanoyloxymethyl group with the alkanoyl moiety having from 1 to 22 carbon atoms such as methanoyloxymethyl to docosanoyloxymethyl groups.

The long alkyl group-bearing spiropyran used as a starting material can be prepared by a known procedure. For instance, a substituted indolenine is reacted with a halogenated hydrocarbon such as iodooctadecane in a solvent under heating conditions to obtain a hydrocarbon-substituted indolenium halide.

The thus substituted indolenium halide is converted into a corresponding indoline by means of an alkali. This indoline is further reacted with a salicylaldehyde having substituents as defined by $R_1$ and $R_2$ in a solvent under heating conditions to obtain a long alkyl group-bearing spiropyran compound. The preparation of the starting spiropyran will be described in more detail in examples appearing hereinafter.

The spiropyran compound is subsequently reacted with a halogenating agent to introduce a halogen atom or atoms into the compound. The halogenation reaction of the spiropyran compound proceeds in a solvent in the absence of any catalyst and the type of halogenated product varies depending on the reaction temperature.

Thus, a halogenated spiropyran compound of the following formula (II) is obtained

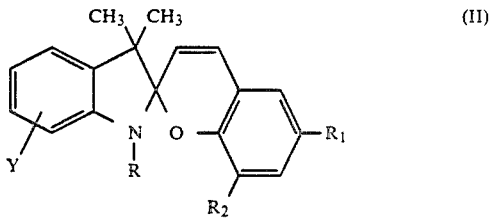

wherein R, $R_1$ and $R_2$ have, respectively, the same meanings as defined above and Y represents fluorine, chlorine, bromine or iodine provided that one to four halogen atoms are substituted at the 4', 5', 6' and/or 7' position of the indoline ring.

Examples of the solvent include tetrahydrofuran, carbon tetrachloride, acetic acid and chloroform, alcohols such as ethanol, and mixtures thereof. As stated above, the type of halogenated product varies depending on the reaction temperature. If the reaction is effected at a temperature of about 0° C., a spiropyran compound having a halogen atom at the 5' position alone, and when the reaction temperature is about 25° C., a dihalo product is obtained. When the reaction temperature is about 50° C., a trihalo product is obtained. Moreover, when the reaction temperature is about 60° C., a tetrahalo product is obtained. The reaction time is generally in the range of from 0.5 to 3 hours.

After completion of the reaction, the reaction mixture is usually neutralized by means of an alkali such as sodium hydroxide, potassium hydroxide, sodium carbonate, potassium carbonate, sodium hydrogencarbonate, potassium hydrogencarbonate or the like, in a solvent such as chloroform, ethyl acetate, benzene or the like. Thereafter, the reaction product is subjected to solvent extraction as usual.

Examples of the halogenating agent include N-halosuccinimides such as N-bromosuccinimide, N-chlorosuccinimide, N-iodosuccinimide and N-fluorosuccinimide, halogens such as $F_2$, $Cl_2$, $Br_2$ and $I_2$, and the like. Of these, N-bromosuccinimide and N-chlorosuccinimide are preferred and, accordingly, Y in the formula (II) is preferably bromine or chlorine. In this connection, the halogen is preferably substituted at the 5' position or at the 5' and 7' positions of the spiropyran compound.

In the halogenation reaction, the halogenating agent is used in an excess amount of from 2 to 5 times by mole as compared to the molar amount of the starting spiropyran.

The reaction product may be purified by any known procedure such a column chromatography, recrystallization, sublimation or the like. These purification techniques may be used in combination.

Although depending on the types of starting spiropyran, halogenating agent and final product, the yield is in the range of from 15 to 80% based on the starting spiropyran.

The present invention is more particularly described by way of examples. A comparative example is also shown.

EXAMPLE 1

One example of preparing a halogenated spiropyran with a long alkyl chain of the following formula is described. This spiropyran is hereinafter abbreviated as "SP-B".

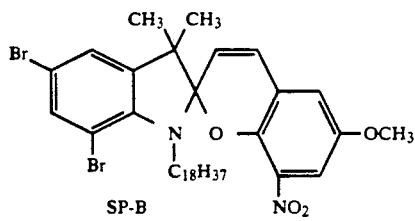

SP-B

Step 1

42.3 g (266 mmols) of 2,3,3-trimethylindolenine of the formula (1) and 101.1 g (266 mmols) of iodooctadecane were dissolved in 200 ml of 2-butanone, followed by refluxing for 40 hours under heating conditions. After removal of the 2-butanone by distillation, the resultant solid matter was recrystallized from 1000 ml of ethanol to obtain 91.5 g (197 mmols, yield 63.9%) of a reddish white solid of 1-octadecyl-2,3,3-trimethylindolenium iodide of the following formula (3).

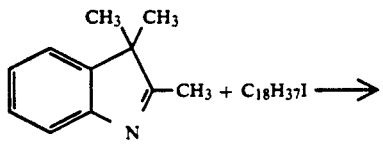

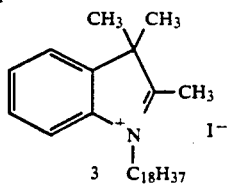

Step 2

91.5 g (197 mmols) of the thus obtained 1-octadecyl-2,3,3-trimethylindolenium iodide of the formula (3) was dispersed in 100 ml of diethyl ether, followed by further dispersion in 400 ml of a 3.8 N sodium hydroxide aqueous solution. After agitation for 2.5 hours, the resultant oil phase was extracted with diethyl ether. After drying with sodium hydroxide over day and night, the diethyl ether was distilled off to obtain 65.6 g (159 mmols, yield 80.7%) of 1-octadecyl-2-methylene-3,3-dimethylindoline of the formula (4). The above reaction is shown below.

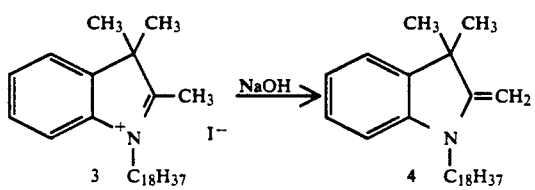

Step 3

8.0 g (52.6 mmols) of 5-methoxysalicylaldehyde of the formula (5) was dissolved in 50 ml of acetic acid. While the reaction solution was violently agitated and kept at about 15° C. by the use of iced water, a solution of 2.5 ml (59.7 mmols) of fuming nitric acid 8d=1.52, 99%) in 8 ml of acetic acid was dropped in 1 hour. The agitation was further continued for 7 hours. The resultant precipitate was filtered and recrystallized from 500 ml of ethanol to obtain 4.2 g (21.3 mmols, yield 40.5%) of yellow needle-like crystals of 3-nitro-5-methoxysalicylaldehyde of the formula (6). This reaction is shown below.

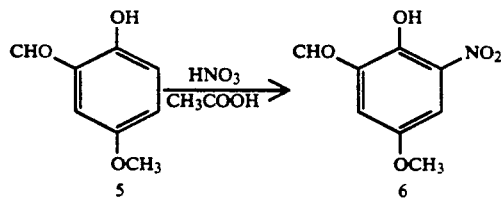

Step 4

2 g (4.9 mmols) of the 1-octadecyl-2-methylene-3,3-dimethylindoline of the formula (4) prepared in the steps 1 and 2 and 0.8 g (4.1 mmols) of the 3-nitro-5-methoxysalicylaldehyde of the formula (6) prepared in the step 3 weer heated in methanol under reflux for 1 hour. The dark green reaction solution was cooled and the resultant precipitate was recrystallized three times with 80 ml of ethanol to obtain 1.6 g (2.7 mmols, yield 65.9%) of spiropyran of the formula (7) as yellowish brown crystals).

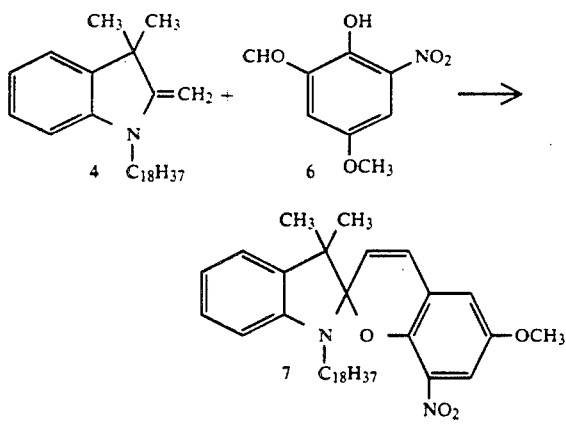

The thus obtained spiropyran was brominated in the following manner.

Step 5

1.1 g (6.0 mmols) of N-bromosuccinimide was dissolved in a mixed solvent of acetic acid and chloroform at a ratio by volume of 1:1. An acetic acid solution of 1.6 g (2.7 mmols) of the spiropyran of the formula (7) was dropped in the above solution in 30 minutes at 25° C. After one hour, the resultant solution was poured into a mixture of chloroform and sodium hydroxide and extracted with chloroform. The organic phase was dried and concentrated, after which it was purified through column chromatography and recrystallized twice from ethanol, thereby obtaining 300 mg of spiropyran (SP-B). The above reaction proceeds as follows.

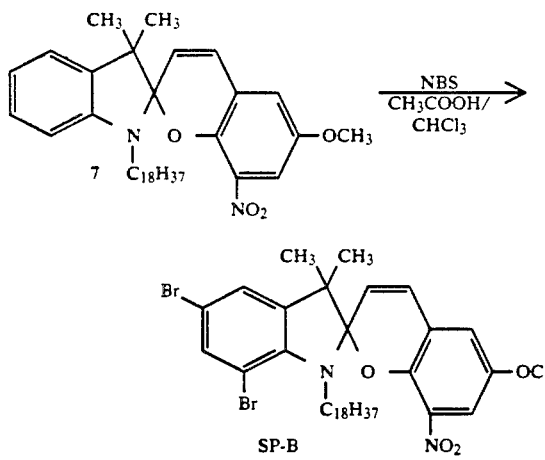

The methanol solution of the colored product of SP-B had a value of $\lambda_{max}$ of 650 nm and had sensitivity to light with a wavelength of 700 nm. When light with a wavelength of 700 nm was applied to the solution, it rapidly turned into a colorless solution.

The SP-B compound had well-balanced hydrophilicity and hydrophobicity and could be formed into a thin film under the following conditions according to the LB method.

Compression speed: 10 mm/minute
Build-up speed: 10 mm/minute
Build-up pressure: 20 mN/m The resultant film had a thickness of 2.5 nm and exhibited photochromism as in the solution. Thus, the photochromism of SP-B was confirmed to be developed in the form of a ultrathin film.

In the above example, the spiropyran compound of the formula (II) wherein $R_1$ is a nitro group and $R_2$ is a methoxy group is described. The process of the invention was not influenced by the types of substituents represented by $R_1$ and $R_2$. The photochromic spiropyran compounds obtained by the invention could be formed into ultrathin films according to the LB method. In the following table, there are shown the values of $\lambda_{max}$ of LB films of spiropyrans of the formula (II) wherein other combinations of substituents represented by $R_1$ and $R_2$ are used.

| R | $R_1$ | $R_2$ | $\lambda_{max}$ |
|---|---|---|---|
| $C_{18}H_{37}$ | $OCH_3$ | $NO_2$ | 650 |
| $C_{18}H_{37}$ | $NO_2$ | $COCH_3$ | 610 |
| $C_{18}H_{37}$ | Br | H | 615 |
| $C_{18}H_{37}$ | $NO_2$ | $CH_2OCOCH_3$ | 620 |

The spiropyran of the formula (II) wherein R is an alkyl group having 18 carbon atoms as in the above example has so good in amphoteric property that film formation by the LB method is very easy. Thus, such spiropyran compounds are preferred. In addition, spiropyran compounds of the formula (II) wherein R represents an alkyl group having from 14 to 22 carbon atoms could be readily obtained using alkyl halides having corresponding numbers of carbon atoms. These compounds was amphoteric in nature and could also be formed into thin films by the LB method. The values of $\lambda_{max}$ of these films were almost the same as those of the spiropyran compounds having the octadecyl group.

When the above steps were repeated using different numbers of carbon atoms as R, spiropyran compounds having not higher than 13 carbon atoms or not less than 23 carbon atoms as R could be prepared.

Bromination could proceed most preferably when using N-bromosuccinimide, but other brominating agents such as bromine could be likewise used.

In the above example, the spiropyran compound had a bromine atom at both 5' and 7' positions.

When the above reaction of step 5 was repeated at 0° C., a monobromo spiropyran at the 5' position obtained. Similarly, triboromo and tetrabromo products were obtained at 50° C. and 60° C., respectively.

COMPARATIVE EXAMPLE

Indolenine bromide and iodooctadecane were dissolved in 2-butanone and heated under reflux for 40 hours. Any reaction did not proceed and the starting materials were collected.

Moreover, when alkyl halides having 6 or more carbon atoms were used instead of indolenine bromide, the reaction did not proceed at all. Although alkyl halides having 5 or less carbon atoms were used, the reaction proceeded slightly with a very low yield.

In view of the above, the process of the invention is very effective in producing spiropyran compounds having both a halogen atom or atoms and a long alkyl chain.

EXAMPLE 2

The general procedure of Example 1 was repeated except that N-chlorosuccinimide was used instead of N-bromosuccinimide in step 5 of Example 1, thereby obtaining the following spiropyran compound, SP-C.

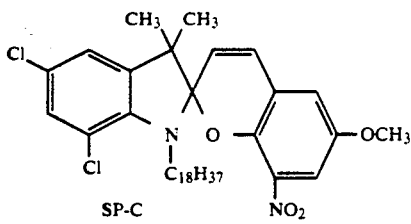

SP-C

A methanol solution of a colored product of SP-C had a value of $\lambda_{max}$ of 650 nm and had a sensitivity to light with a wavelength of 700 nm. When the solution was irradiated with visible light with a wavelength of 700 nm, it rapidly turned into a colorless product. This spiropyran compound was built up by the LB method, like the compound of Example 1 and the built-up film exhibited photochromism.

In these examples, bromination and chlorination are stated. When a fluorinating agent such as fluorine and an iodizing agent such as iodine were used, fluorination and iodination could be likewise conducted.

What is claimed is:

1. A process for preparing a photochromic halogenated spiropyran compound having a hydrophobic alkyl chain wherein said spiropyran compound is of the following formula (II)

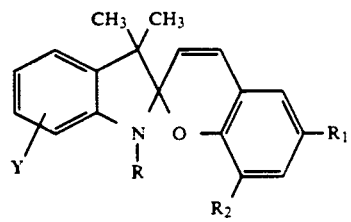

wherein R, $R_1$ and $R_2$ have, respectively, the same meanings as defined above and Y represents fluorine, chloride, bromine or iodine provided that one to four halogen atoms are substituted at the 4', 5', 6' and/or 7' position of the indoline ring the process comprising
providing a photochromic spiropyran compound of the following formula (I)

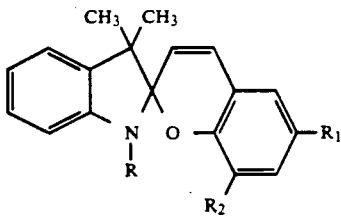

wherein R is an alkyl group, and $R_1$ and $R_2$ independently represent hydrogen, a ketoalkyl, an alkoxy group, a nitro group, a halogen atom or an alkanoyloxymethyl group; and
reacting a halogenating agent directly with the spiropyran compound of formula (I) at a temperature from about 0° C. to about 60° C. to obtain said halogenated spiropyran photochromic compound according to formula (II) above.

2. A process according to claim 1, wherein said halogenating agent is an N-bromosuccinimide and Y in the formula (II) is bromine.

3. A process according to claim 2, wherein said bromine is substituted at the 5' and 7' positions.

4. A process according to claim 2, wherein said bromine is substituted at the 5' position.

5. A process according to claim 1, wherein said halogenating agent is an N-chlorosuccinimide and Y in the formula (II) is chlorine.

6. A process according to claim 5, wherein said chlorine is substituted at the 5' and 7' positions.

7. A process according to claim 5, wherein said chlorine is substituted at the 5' position.

8. A process according to claim 1, wherein said alkyl group represented by R has not less than 6 carbon atoms.

9. A process according to claim 8, wherein said alkyl group has from 14 to 22 carbon atoms.

10. A process according to claim 8, wherein said alkyl group has 18 carbon atoms.

11. A process according to claim 1, wherein said spiropyran compound is of the following formula

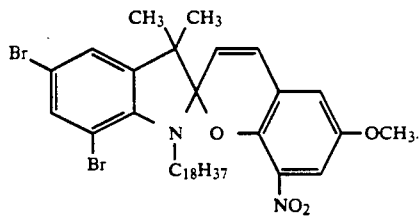

12. A process according to claim 1, wherein said spiropyran compound is of the following formula

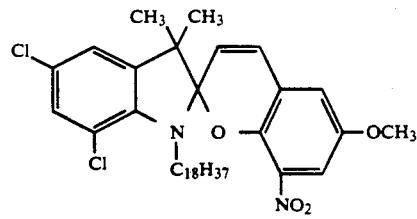

* * * * *